United States Patent [19]
Trepanier et al.

[11] 3,933,833
[45] Jan. 20, 1976

[54] PHENYL -THIOUREA, -CARBOTHIOAMIDE AND -CARBONOTHIOAMIDE DERIVATIVES

[75] Inventors: Donald L. Trepanier; Thomas C. Britton, both of Midland, Mich.

[73] Assignee: The Dow Chemical Company, Midland, Mich.

[22] Filed: May 30, 1974

[21] Appl. No.: 474,506

[52] U.S. Cl. .................. 260/293.73; 260/326.5 S; 260/552 R; 260/552 SC; 424/267; 424/274; 424/322; 424/323
[51] Int. Cl.² ................................. C07D 211/42
[58] Field of Search..... 260/293.73, 326.5 S, 552 R, 260/552 SC

[56] References Cited
UNITED STATES PATENTS 3,188,312    6/1965    Gundel et al. ............... 260/552 R
3,767,816    10/1973    Moss et al. .................. 424/322

OTHER PUBLICATIONS

Chemical Abstracts 67: 32401f (1967), Dovlatyan et al.

*Primary Examiner*—Sherman D. Winters
*Attorney, Agent, or Firm*—Maynard R. Johnson; Gary D. Street

[57]    ABSTRACT

Disclosed are various phenyl -thiourea, -carbothioamide and -carbonothioamide derivatives which are useful in alleviating symptoms and conditions of inflammation.

9 Claims, No Drawings

PHENYL -THIOUREA, -CARBOTHIOAMIDE AND -CARBONOTHIOAMIDE DERIVATIVES

SUMMARY OF THE INVENTION

The present invention is directed to phenyl -thiourea, -carbothioamide and -carbonothioamide derivatives selected from the group consisting of N-(2,4-dimethylphenyl)-3-hydroxy-1-pyrrolidinecarbonothioamide (hereinafter, Compound A), N-(2,4-dimethylphenyl)-3-hydroxy-1-piperidinecarbonothioamide (Compound B), N-(2,4-dimethylphenyl)-N'-(2-hydroxypropyl) thiourea (Compound C), N-(2,4-dimethylphenyl)-N'-(3-hydroxypropyl) thiourea (Compound D), N-(2-(dimethylamino) ethyl)-N'-(2,4-dimethylphenyl)thiourea (Compound E), N-(2,4-dimethylphenyl)-N'-(2-methoxyethyl)thiourea (Compound F), N-(2,4-dimethylphenyl)-N'-(2-ethoxyethyl)thiourea (Compound G), N'-(2,4-dimethylphenyl)-N-ethyl-N-(2-hydroxyethyl)thiourea (Compound H), N-(2-(diethylamino)ethyl)-N'-(2,4-dimethylphenyl)thiourea (Compound I), 2-(2-hydroxy-2-methylpropyl)-2-methyl-N-phenylhydrazinecarbothioamide (Compound J), N-(2,4-dimethylphenyl)-1-(2-hydroxyethyl) hydrazinecarbothioamide (Compound K), N-(2,2-dimethoxyethyl)-N'-(2,4-dimethylphenyl-thiourea (Compound L) and N-(2,4-dimethylphenyl)-N'-(2-hydroxy-2phenylethyl)thiourea (Compound M). For convenience, the above compounds will hereinafter be referred by using the designated letters A – M, respectively.

Compounds C, E, G, H and I constitute a preferred class of compound, in the present invention. In a further embodiment, Compounds A and B are preferred. In an additional embodiment of the present invention, Compounds F and G are especially preferred.

The compounds of the present invention are generally prepared by the reaction of a selected phenyl isocyanate reactant with a selected amine reactant. The reaction is usually carried out, with agitation, in the presence of an inert carrier medium, such as, for example, ethanol, isopropanol, benzene, chloroform, dimethoxyethane and the like, and a solution of the isocyanate reactant with a portion of the carrier medium is ordinarily added portionwise to a solution of the amine reactant in the carrier medium. While the amounts of reactants employed are not critical, equimolar amounts are usually employed. Following the completion of the isocyanate reactant addition, the reaction mixture is agitated at temperatures of from about 20° to about 80° C. for a period of from about 6 to about 30 hours. Following such, period, the desired product is recovered from the reaction mixture by employing conventional procedures. Ordinarily, the product precipitates from the reaction mixture and is recovered by filtration and purified by recrystallization from a suitable solvent, such as, alcohols, for example, isopropanol, ethanol or the like or washed with isopropanol, ether-hexane mixtures or the like. In other methods, the solvent is removed from the reaction mixture in vacuo to obtain the desired product as a crystalline solid or a residual oil which solidifies on standing or which can be mixed with a suitable solvent, such as an ether, and the product crystallized therefrom.

The following examples illustrate in greater detail the preparation of typical compounds.

EXAMPLE 1

A solution of phenyl isothiocyanate (27.0 grams; 0.2 mole) in about 100 milliliters (ml.) of benzene was added dropwise to an agitated solution of 2-(2-hydroxy-2-methylpropyl)-2-methylhydrazine (23.6 grams; 0.2 mole) in about 200 ml. of benzene. Following the completion of the addition, the resulting reaction mixture was stirred at reflux temperatures for about 17 hours. Following such period, the reaction mixture was cooled. The resulting white product precipitate was recovered by filtration, washed with benzene and dried under vacuum. As a result of such operations, the desired 2-(2-hydroxy-2-methylpropyl)-2-methyl-N-phenylhydrazine-carbothioamide product was recovered as a white solid having a melting point of 125°–127°C.

EXAMPLE 2

A solution of 2,4-dimethylphenylisothiocyanate (8.2 grams; 0.05 mole) in about 70 ml. of isopropanol was added dropwise to an agitated solution of 3-hydroxy-1-pyrrolidine (4.4 grams; 0.05 mole) in about 70 ml. of isopropanol. The resulting reaction mixture was stirred at ambient temperatures for a period of about 24 hours. The reaction mixture was then cooled and filtered to remove the white product precipitate, which was washed with cold isopropanol and dried at about 60°C. As a result of such operations, the desired N-(2,4-dimethylphenyl)-3-hydroxy-1-pyrrolidinecarbonothioamide was obtained as an off-white solid having a melting point of 164°–166°C.

EXAMPLE 3

A solution of 2,4-dimethylphenylisothiocyanate in about 70 ml. of benzene was added dropwise to an agitated solution of 3-hydroxypropylamine (3.8 grams) in about 80 ml. of benzene. The resulting reaction mixture was maintained, with stirring, at ambient temperatures for about 16 hours. Following such period, the benzene in the reaction mixture was removed in vacuo and the residual oil triturated with ethyl ether and the desired product crystallized therefrom and washed again with ethyl ether. As a result of such operations, the desired N-(2,4-dimethylphenyl)-N'-(3-hydroxypropyl)-thiourea product was obtained as a white solid having a melting point of 90°–93°C.

The other compounds of the present invention were similarly obtained according to the procedures and teachings of the foregoing examples and specification. The phenylisothiocyanate reactants are known materials and can readily be prepared by those skilled in the art. The following example is representative of the preparation of such materials.

EXAMPLE 4

A solution of 2,4-dimethylaniline (315 grams; 2.6 moles) in about 1.2 liters of $CHCl_3$ was added dropwise over a period of about 15 minutes to a cooled and agitated solution of thiophosgene (300 grams; 2.6 moles) in about 1.5 liters of water. Following the completion of the addition the reaction mixture was stirred at ambient temperatures for about one hour and the organic and aqueous layers subsequently separated. The aqueous layer was extracted with $CHCl_3$ and the extracts combined with the $CHCl_3$ organic product layer and dried over magnesium sulfate. The organic layer was then evaporated in vacuo and the residual brown oil was distilled at 141°–149°C. and 15 millimeters of mercury to yield a yellow oil, representing the desired 2,4-dimethylphenylisothiocyanate intermediate, which solidified on standing.

The compounds of the present invention possess antiinflammatory activity and methods of alleviating or preventing symptoms or conditions of inflammation in a mammal suffering from an inflammatory condition are accordingly included within the scope of the present invention. The compounds of the present invention are administered internally, i.e., orally or parenterally. Such compounds can be formulated into various pharmaceutical dosage forms such as tablets, capsules, solutions, suspensions, pills and the like, for immediate or sustained release, by combining the active compounds with suitable pharmaceutically acceptable carriers or diluents according to methods well known in the art. Such dosage forms may additionally include excipients, binders, fillers, flavoring and sweetening agents and other therapeutically inert ingredients necessary in the formulation of the desired pharmaceutical preparation. Various diluents, dosage forms, and other variations and modifications are well within the ability of those skilled in the art. Such ramifications are deemed to be within the scope of this invention.

For oral administration, pharmaceutical preparations of this invention may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders capsules, slurries and the like and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or codliver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweetening agents, flowing agents, coloring materials and preservatives.

For parenteral use, the compounds of this invention can be formulated with sterile ingredients compounded and packaged asceptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g., at least 1 percent and preferably at least 5 percent, are preferred as they allow for the easier administration of the compound.

The method of treating inflammation in accordance with this invention comprises administering internally to a mammal a compound as represented by Formula I, usually combined with a pharmaceutical excipient or carrier, in an amount sufficient to produce an antiinflammatory effect. Preferably, the compounds are administered orally. Advantageously, the equal doses will be administered from one to six times daily.

The dosage required to achieve antiinflammatory activity in the animal will vary with various factors such as the species of animals, general health and tolerances of the animal, weight, sex and age of the animal, the nature and severity of the disease being treated and the like. Additionally, it is to be noted that the exact dosage of each individual compound employed in similar situations will vary. Generally, a total daily dosage would be in the range of from about 5.0 to about 150.0 milligrams or more per kilogram of body weight, usually from 15.0 to about 75.0 milligrams per kilogram of body weight.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

The antiinflammatory activity of the compounds of the present invention was determined in procedures analagous to the method of Winter et al described in "Proceedings of the Society For Experimental Biology and Medicine," vol. 111, p. 544 (1962). In such operations, edema is induced by injection into the plantar surface of the right hind paw of a rat of carrageenin, prepared as a 1 percent suspension in sterile glass distilled water. The volume injected is 0.1 ml. The volume of the paw is measured immediately after injection with carrageenin and again three hours later. The difference in volume between the two measurements indicates the increase due to swelling caused by edematous fluid. Rat paw volume is measured by plethesmography. The percent decrease in milliliters displaced as compared to untreated controls is expressed as percent inhibition of edema.

One hour before injection with carrageenin the test animals are orally administered the test ingredient suspended (or dissolved) in 0.5% carboxymethylcellulose (1 ml./100 grams) and sufficient water to equal a total volume of 5 mls.

The following table shows the percentage of inhibition of inflammation by representative compounds of the present invention. All compounds were administered at a dosage rate of 60 mg./kg.

TABLE I

| Test Compound | Inhibition of Edema, percent |
|---|---|
| A | −41.1 |
| B | −19.6 |
| C | −22.2 |
| D | −27.8 |
| E | −14.6 |
| F | −69.2 |
| G | −67.7 |
| H | −27.0 |
| I | −22.9 |
| J | −21.6 |

Other compounds of the present invention are similarly found to be active at various dosage rates.

While the present invention has been illustrated with the aid of certain specific embodiments thereof, it will be readily apparent to those skilled in the art that the invention is not limited to those particular embodiments, and that various changes and modifications may be made without departing from the spirit of the present invention or the scope of the appended claims.

What is claimed is:

1. A compound selected from the group consisting of N-(2,4-dimethylphenyl)-3-hydroxy-1-pyrrolidinecarbonothioamide, N-(2,4-dimethylphenyl)-3-hydroxy-1-piperidinecarbonothioamide, N-(2,4-dimethylphenyl)-N'-(2-methoxyethyl)thiourea, N-(2,4-dimethylphenyl)-N'-(2-ethoxyethyl)thiourea, 2-(2-hydroxy-2-methylpropyl)-2-methyl-N-phenylhydrazinecarbothioamide, N-(2,4-dimethylphenyl)-1-(2-hydroxyethyl)-hydrazinecarbothioamide, N-(2,2-dimethoxyethyl)-N'-(2,4-dimethylphenyl)thiourea and N-(2,4-dimethylphenyl)-N'-(2-hydroxy-2-phenylethyl)thiourea.

2. The compound according to claim 1 which is N-(2,4-dimethylphenyl)-3-hydroxy-1-pyrrolidinecarbonothioamide.

3. The compound according to claim 1 which is N-(2,4-dimethylphenyl)-3-hydroxy-1-piperidinecarbonothioamide.

4. The compound according to claim 1 which is N-(2,4-dimethylphenyl)-N'-(2-methoxyethyl)thiourea.

5. The compound according to claim 1 which is N-(2,4-dimethylphenyl)-N'-(2-ethoxyethyl)thiourea.

6. The compound according to claim 1 which is 2-(2-hydroxy-2-methylpropyl)-2-methyl-N-phenylhydrazinecarbothioamide.

7. The compound according to claim 1 which is N-(2,4-dimethylphenyl)-1-(2-hydroxyethyl)hydrazinecarbothioamide.

8. The compound according to claim 1 which is N-(2,2-dimethoxyethyl)-N'-(2,4-dimethylphenyl)thiourea.

9. The compound according to claim 1 which is N-(2,4-dimethylphenyl)-N'-(2-hydroxy-2-phenylethyl)thiourea.

* * * * *

UNITED STATES PATENT AND TRADEMARK OFFICE
CERTIFICATE OF CORRECTION

PATENT NO. : 3933833
DATED : January 20, 1976
INVENTOR(S) : Donald L. Trepanier, Thomas C. Britton It is certified that error appears in the above–identified patent and that said Letters Patent are hereby corrected as shown below:

Column 1, line 29, "2phenylethyl)thiourea" should read --2-phenylethyl)thiourea--;

Column 2, line 62, "addition the reaction mixture" should read --addition, the reaction mixture--;

Column 3, line 41, "powders capsules," should read --powders, capsules,--.

Signed and Sealed this

Twenty-fourth Day of August 1976

[SEAL]

Attest:

RUTH C. MASON
Attesting Officer

C. MARSHALL DANN
Commissioner of Patents and Trademarks